United States Patent [19]

Schwartz

[11] Patent Number: 5,073,497
[45] Date of Patent: Dec. 17, 1991

[54] MICROBEAD REFERENCE STANDARD AND METHOD OF ADJUSTING A FLOW CYTOMETER TO OBTAIN REPRODUCIBLE RESULTS USING THE MICROBEADS

[75] Inventor: Abraham Schwartz, Hato Rey, P.R.

[73] Assignee: Caribbean Microparticles Corporation, Hato Rey, P.R.

[21] Appl. No.: 465,792

[22] Filed: Jan. 16, 1990

Related U.S. Application Data

[63] Continuation-in-part of Ser. No. 374,435, Jun. 30, 1989, which is a continuation-in-part of Ser. No. 128,786, Dec. 4, 1987, Pat. No. 4,857,451, which is a continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.$^5$ .................. G01N 31/00; G01J 3/30; G01J 1/02
[52] U.S. Cl. ........................... 436/8; 436/10; 356/318; 356/243
[58] Field of Search ..................... 436/8-18, 436/63; 252/408.1; 356/318, 243

[56] References Cited

U.S. PATENT DOCUMENTS

| | | | |
|---|---|---|---|
| 4,035,316 | 7/1977 | Yen | 260/2.5 |
| 4,157,323 | 6/1979 | Yen | 260/29.7 |
| 4,162,282 | 7/1979 | Fulwyler et al. | 436/10 |
| 4,247,434 | 1/1981 | Vanderhoff | 260/29.6 |
| 4,254,096 | 3/1981 | Monthony | 424/8 |
| 4,438,239 | 3/1984 | Rembaum | 525/54.1 |
| 4,511,662 | 4/1985 | Baran | 436/513 |
| 4,552,633 | 11/1985 | Kuma Kura | 204/159 |
| 4,605,630 | 8/1986 | Kung | 436/511 |
| 4,609,689 | 9/1986 | Schwartz | 523/202 |
| 4,656,144 | 4/1987 | Hosaka | 436/534 |
| 4,665,020 | 5/1987 | Saunders | 405/7 |
| 4,694,035 | 9/1987 | Kasai | 524/458 |
| 4,698,262 | 10/1987 | Schwartz | 428/402 |
| 4,699,826 | 10/1987 | Schwartz | 428/402 |
| 4,699,828 | 10/1987 | Schwartz | 428/402 |
| 4,714,682 | 12/1987 | Schwartz | 436/10 |
| 4,751,188 | 6/1988 | Valet | 436/63 |
| 4,767,206 | 8/1988 | Schwartz | 436/10 |
| 4,774,189 | 9/1988 | Schwartz | 436/10 |
| 4,828,984 | 5/1989 | Schwartz | 435/7 |
| 4,857,451 | 8/1989 | Schwartz | 436/10 |
| 4,868,126 | 9/1989 | Schwartz | 436/19 |
| 4,918,004 | 4/1990 | Schwartz | 436/10 |

OTHER PUBLICATIONS

Webster's 9th New Collegiate Dictionary.

Primary Examiner—David L. Lacey
Assistant Examiner—William Chan
Attorney, Agent, or Firm—Olive & Olive

[57] ABSTRACT

A flow cytometer reference standard containing a highly uniform microbead population, wherein each microbead has the same multiple fluorescent labels as the other microbeads and as the samples to be measured. Target conditions are set for the sample after alignment of the flow cytometer. The microbead reference standard is used to determine peak channels (target channels) for each parameter. The target conditions may be reestablished for later uses of the flow cytometer with the same type of samples by using the microbead reference standard to adjust the flow cytometer so that the microbead peak channels fall in the originally determined target channels.

19 Claims, 4 Drawing Sheets

MICROBEAD REFERENCE STANDARD AND METHOD OF ADJUSTING A FLOW CYTOMETER TO OBTAIN REPRODUCIBLE RESULTS USING THE MICROBEADS

CROSS-REFERENCE TO RELATED APPLICATIONS

This application is a continuation-in-part of U.S. application Ser. No. 07/374,435 filed June 30, 1989; which is a continuation-in-part of U.S. application Ser. No. 07/128,786 filed Dec. 4, 1987, issued August 15, 1989 as U.S. Patent No. 4,857,451; which is a continuation-in-part of U.S. application Ser. No. 06/805,654 filed Dec. 11, 1985, issued Sept. 27, 1988 as U.S. Pat. No. 4,774,189, which in turn is a continuation-in-part of U.S. application Ser. No. 06/685,464 filed Dec. 24, 1984, issued Aug. 30, 1988 as U.S. Pat. No. 4,767,206.

BACKGROUND OF THE INVENTION

1. Field of the Invention

This invention relates generally to a method for a multiple fluorescent channel flow cytometer for subsequent analysis of samples, and in particular, to the use of microbeads with multiple fluorescent labels that serve as a reference for forward scatter and for fluorescence intensity for a plurality of fluorescent dyes.

2. Description of the Art

Flow cytometers are used to analyze biological cells and particles present in a fluid sample by intersecting a thin stream of the fluid by an illumination source, usually a laser beam. The resulting forward and right angle scattered and fluorescent light is analyzed with photomultiplier tubes (PMTs). The fluorescent channels of a flow cytometer, designated by Fl1, Fl2, Fl3 etc., are each set with barrier filters to detect a selected specific dye while filtering out signals from dyes that fluoresce at other wavelengths.

As discussed in the co-pending parent patent application, flow cytometers must be aligned and calibrated to obtain accurate, reproducible results. When more than one fluorescent dye is used, the instruments also require compensation for the fluorescence PMTs.

Alignment is the process of adjusting and focusing the optical and electrical components of the flow cytometer including the laser, lenses, mirrors barrier filters and PMTs, so that scatter and fluorescence signals have the lowest coefficient of variation of distribution (CV). Alignment of a flow cytometer can be determined by a dot plot of the forward and right angle scatter channels a shown by comparison of the dot plots of FIG. 1 (an unaligned instrument) and FIG. 2 (an aligned instrument).

Compensation is the process of electronically removing residual signals from fluorescent dyes in secondary fluorescence channels due to spectral overlaps no removed by barrier filters for the respective channels. Use of the flow cytometer's compensation circuits at an appropriate level changes the dot plot for the fluorescent channel Fl1 versus the fluorescent channel Fl2 from that shown in FIG. 3 (fluorescent microbeads (2) and (3) overlapping the boundaries designated by blank microbeads (1)) to that shown in FIG. 4 (the dot group is aligned with a blank or unlabeled sample in the secondary fluorescence channel). If the compensation is set too high, data from the sample may be lost (FIG. 5).

To perform accurate analysis with two or more fluorescent dyes, the electrical compensation circuit must be adjusted so that fluorescence emission which overlaps into other fluorescence channels may be subtracted from these other channels. For example, when fluorescein (FITC) and phycoerythrin (PE) are simultaneously employed as the fluorescent dyes, the green fluorescence channel for fluorescein may have a band pass emission filter of $520 \pm 10$ nanometers (nm) and the red fluorescence channel for phycoerythrin may have a band pass emission filter of $580 \pm 10$ nm. The emission spectrum of fluorescein is such that part of its fluorescence will be seen in the phycoerythrin fluorescence channel of $580 \pm 10$ nm, and to a lesser degree, part of the emission of phycoerythrin will appear in the fluorescein fluorescence channel of $520 \pm 10$ nm.

A particular problem associated with numerous samples measured by flow cytometry relates to naturally occurring fluorescence, i.e., autofluorescence, of the sample. For example, a wide variety of biological cells contain naturally occurring fluorescent compounds such as riboflavin. Such autofluorescence introduces an additional complexity to the flow cytometer compensation process, and tends to promote miscompensation (over-and/or under-compensation) in the respective fluorescence channels of the flow cytometer.

In co-pending application Ser. No. 07/374,435, the compensation circuits are adjusted such that the level of fluorescence in the fluorescence channels, other than the channel designated for particular fluorescent dye (the primary channel(s), is equal to the level of fluorescence of the sample prior to labeling the sample with fluorescent dyes. Autofluorescent microbeads, matching the fluorescence spectra and intensity of the unlabeled, naturally fluorescent sample to be measured, are run on the flow cytometer in the Fl1 versus Fl2 fluorescence channel dot plot or histogram display mode. The disclosure of the co-pending application and all patents and applications referred to herein are incorporated herein by reference.

Calibration of a flow cytometer with proper standards ensures that the results from samples will be comparable over time and between different instruments. For the calibration of the intensity of fluorescence signals to be independent of the specific instrument and instrument settings, the excitation and emission spectra of the calibration standards and of the samples being measured must be equivalent and the measurements on each must be made under the same instrument settings. In addition, as described in U.S. Pat. Nos. 4,714,682; 4,767,206; 4,774,189; 4,857,451; and copending U.S. applications Ser. Nos. 109,214 and 374,435, the disclosures of which hereby are incorporated by reference, when the calibration is made in terms of number of equivalent soluble fluorescent molecules, such correction factors, such as quenching and changes in extinction coefficient due to conjugation to other molecules, need not be taken into consideration.

Fluorescence calibration curves for flow cytometers may be constructed by plotting the mean or modal channels of the fluorescence intensity histograms of fluorescence microbead standards against the calibrated values of the number of equivalent soluble fluorescent dye molecules for the respective microbead standards, as shown in FIG. 6.

Although both small (0.1–2 microns) and large (2–50 microns) highly uniform microbeads are readily commercially available from a number of manufacturing companies, e.g., Seragen, Inc., Polysciences, Inc., and Interfacial Dynamics Corp. or have been described (U.S. Pat. Nos. 4,247,434 and 4,336,173), and the synthesis of fluorescent microbeads is taught in U.S. Pat. Nos. 4,157,323 and 4,179,685, fluorescent microbeads have not intended been used as uniform standards with multiple fluorescent labels on each microbead to adjust a flow cytometer for repeated use with a particular sample.

A kit of microbeads that match labeled cells is commercially available under the trademark CaliBrites TM from Becton Dickinson & Co. (Mountain View, Calif.), which consists of three microbead populations: (i) an unlabeled population, (ii) a fluorescein-labeled population, and (iii) a hycoerythrin-labeled population. None of these microbeads are calibrated in any way, and they are intended for standardization of a flow cytometer so that it provides repeatable, reproducible results with the same sample and dyes.

It is therefore a object of the present invention to provide a method for adjustment of a flow cytometer for analysis of selected samples, which may also comprise samples with multiple fluorescent labels, utilizing a single microbead population and enabling the flow cytometer to operate at high efficiency with respect to fluorescence data generated thereby, and in a manner achieving reproduceability of data which is independent of the specific instrument and time-frame of the data measurement and of the compensation of the instrument.

It is another object of the invention to provide a microbead reference standard and a kit having a single microbead population for carrying out such adjustment method.

Other objects and advantages of the invention will be more fully apparent from the ensuing disclosure and appended claims.

SUMMARY OF THE INVENTION

The present invention relates in one aspect to a method of adjusting a flow cytometer, for subsequent measurement of a selected sample which is labeled with fluorescent dyes for measurement of the sample in multiple fluorescence channels of the flow cytometer. The invention relates in another aspect to a kit useful for carrying out such method, which contains one population of highly uniform size microbeads (i.e., $\leq 2\%$ coefficient of variation of diameter) with multiple fluorescent labels on each microbead.

A preferred embodiment of the invention comprises:

A microbead reference standard for adjustment of a flow cytometer, for subsequent measurement of a selected sample comprising cells or particles, said cells or particles labeled with fluorescent dyes, in multiple fluorescence channels of the flow cytometer, said standard comprising a population of microbeads, wherein each of said microbeads:

(a) is labeled with at least two fluorescent dyes that are the same, and have the same fluorescent spectra, as the dyes with which the sample cells or particles are labeled;

(b) is characterized by fluorescence intensity levels registerable in multiple fluorescent channels of a flow cytometer;

(c) is of substantially similar size to the other microbeads in the population, said microbead population having a coefficient of variation of diameter of about 2% or less; and (d) is substantially equivalent in size to the fluorescently labeled cells or particles of the sample.

The kit aspect of the invention broadly relates to a microbead standards kit for adjustment of a flow cytometer, for subsequent measurement of a selected sample which is labeled with fluorescent dyes for measurement of the sample in multiple fluorescence channels of the flow cytometer. Such kit comprises a population of highly uniform same-sized microbeads having a coefficient of variation of diameter of about 2% or less; said microbeads being substantially equivalent in size to the fluorescently labeled sample to be measured by the flow cytometer; each of said microbeads fluorescently labeled with at least two fluorescent dyes and being characterized by fluorescence intensity levels registerable in multiple fluorescent channels of a flow cytometer.

With the kit of the invention, the microbeads may be used to adjust multiple channels of a flow cytometer. The general size and fluorescence properties of the individual microbeads are as described in U.S. Pat. Nos. 4,714,682; 4,767,206; 4,774,189 and 4,857,451.

With this labeling, the excitation and emission spectra of the labeled microbead population matches that of the labeled samples. For example, if lymphocytes are labeled with monoclonal antibodies conjugated to fluorescein and R-phycoerythrin, about 8u diameter microbeads labeled with FITC and R-phycoerythrin would produce the same forward scatter and fluorescence spectra as the labeled lymphocytes.

A doubly-labeled population of microbeads is used as a reference standard for flow cytometers by adjusting the instrument so that the peak channel of the population is always in the same position in each of the four parameters—the forward light scatter, side light scatter, Fl1 green fluorescence and Fl2 red fluorescence. Measurement in any of these parameters for samples of the same size and having the same labels will then be comparable between instruments and over time.

The microbead population in this kit allows the flow cytometer to be adjusted to enable the instrument to yield accurate comparable data.

DETAILED DESCRIPTION OF THE INVENTION, AND PREFERRED EMBODIMENTS THEREOF

Figure 1:
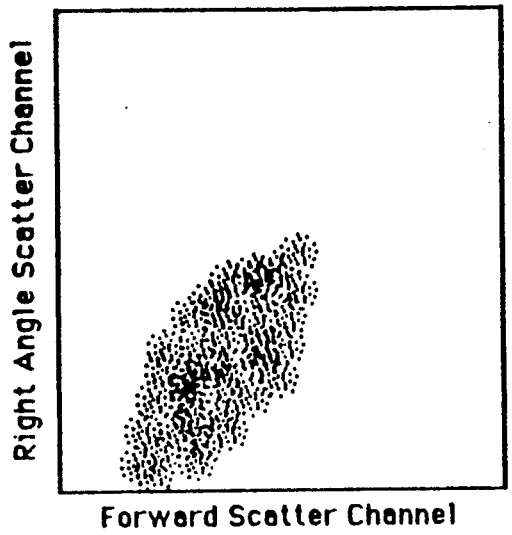
FIG. 1 is a forward versus right angle dot plot for a flow cytometer which is not aligned.
Figure 2:
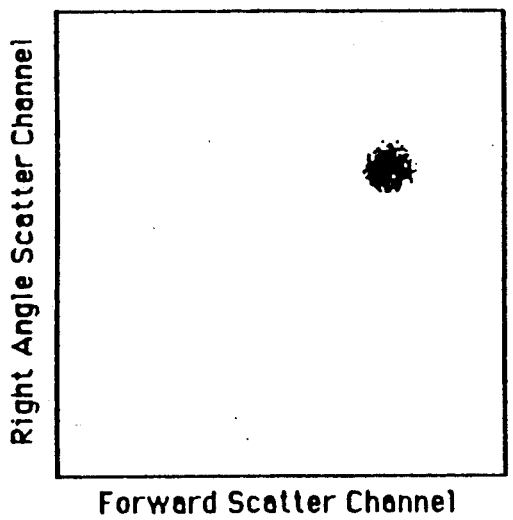
FIG. 2 is a forward versus right angle dot plot for a flow cytometer which is aligned.
Figure 3:
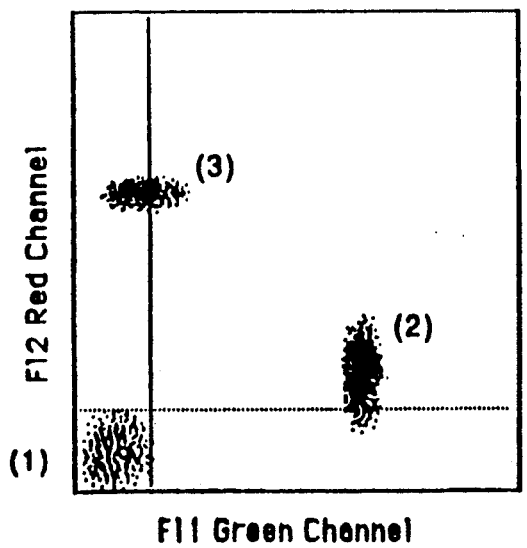
FIG. 3 is a dot plot of the green fluorescence channel Fl1 versus the red fluorescence channel Fl2 of a flow cytometer with its compensation circuits turned off. Dot populations represent (1) blank microbeads, (2) green fluorescent microbeads, and (3) red fluorescent microbeads, as do the same parenthetic numbers in FIG. 4.
Figure 4:
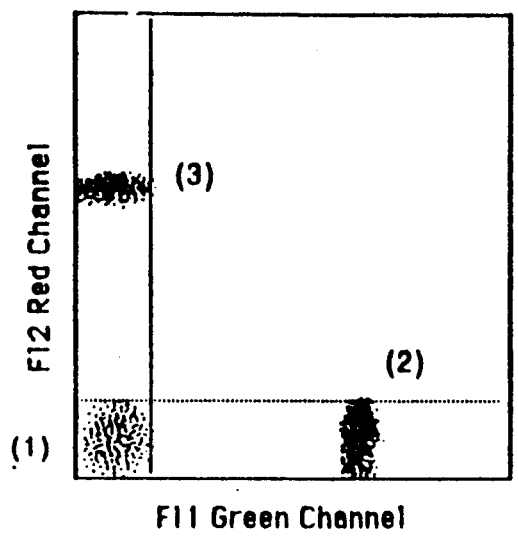
FIG. 4 is a dot plot of the green fluorescence channel Fl1 versus the red fluorescence channel Fl2 of a flow cytometer with its compensation circuits turned on and properly adjusted.
Figure 5:
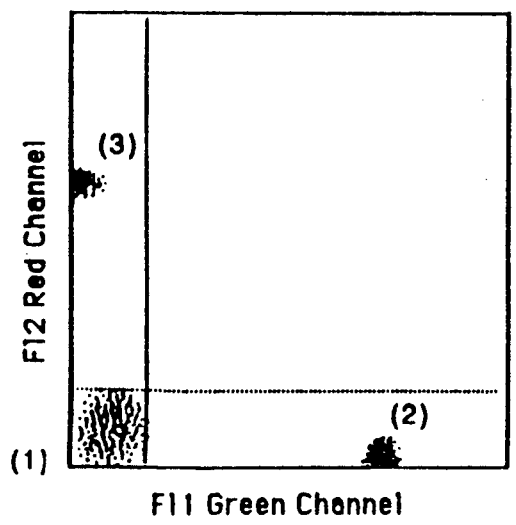
FIG. 5 is a dot plot of the green fluorescence channel fl1 versus the red fluorescence channel Fl2 of a flow cytometer with its compensation circuits adjusted too high, resulting in loss of data or inaccurate data from the samples being measured.
Figure 6:
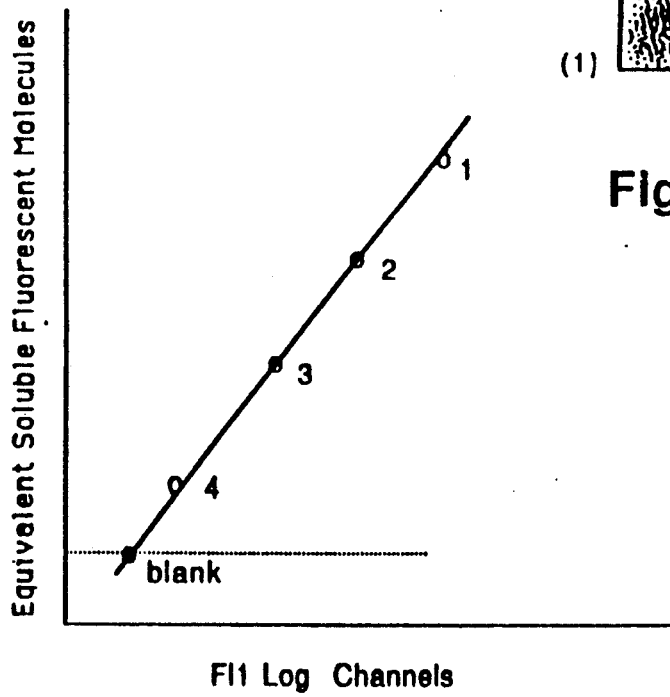
FIG. 6 is a calibration plot of the green fluorescence channel Fl1 of a flow cytometer, wherein number 1-5 indicate modal peak channels of microbead populations of decreasing fluorescence intensity, and the blank microbead indicates the sensitivity level of the instrument in that channel.

The microbead standards kit useful in the broad practice of the invention contains a population of highly uniform same-sized microbeads having a coefficient of variation (CV) of diameter of about 2% or less. The microbeads are substantially equivalent in size to the fluorescently labeled cells or particles in the sample to be measured such as particular blood cells, e.g., 2-20 microns in diameter, so as to fall within the forward and right angle dot plot range of the cell or particle samples being measured. Each microbead is fluorescently labeled with at least two fluorescent dyes and is characterized by fluorescence intensity levels registerable in multiple fluorescent channels of a flow cytometer.

The microbeads are labeled according to methods known in the art and/or disclosed in applicant's previously filed patent applications as referenced herein and incorporated herein by such reference. For example, methyl methacrylate-glycidyl methacrylate or styrene-glycidyl methacrylate microbeads are synthesized and labeled externally with a plurality of fluorescent dyes as discussed in the copending application and previous applications referenced and incorporated herein.

Examples of dye combinations that have been used on microbeads of the invention include: (a) fluorescein and phycoerythrin; (b) allophycocyanine and fluorescein; (c) propidium iodide (PI) and fluorescein; (d) fluorescein and the fluorochrome Hoechst 33342 (Hoechst, Aktiengesellschaft, Frankfurt, West Germany); and (e) TEXAS RED TM (a sulfonyl chloride derived from sulforhodamine 101) (Molecular Probes, Inc., Eugene, Oreg.) and Hoechst 33342. Generally, the fluorescent dye is attached to the surface of the microbead, but the dye, for example, Hoechst 33342 or propidium iodide, may also be incorporated into the body of the microbeads via diffusion of the fluorochrome into the microbeads after dissolution of the dye in a solvent such as methanol.

With the single microbead population of this invention that has the same multiple fluorescence labels on each microbead, the flow cytometer is first aligned. The flow cytometer may be calibrated according to previously disclosed methods as required for the particular instrument and sample.

As discussed below, after the alignment, target conditions are set and target channels determined. The target conditions are redetermined through reestablishing the target channels with the dual-labeled microbeads of the present invention for subsequent instrument use.

The instrument is compensated according to previously known or described methods. Because the level of dye is so high on the microbeads of the invention, the flow cytometer may be compensated at any time in the use of the flow cytometer without interfering with the reproducibility and usefulness of the invention.

(1) Alignment of the Flow Cytometer

The flow cytometer may be aligned by first choosing the instrument parameters, e.g., excitation wavelength, emission barrier filters, amplifiers (linear or log), and signal gains to be used with the samples to be measured. Adjustment of the various optical and electronic components of the flow cytometer then is carried out, as directed by the manufacturer, such that the instrument indicates maximum forward and right angle scatter and fluorescence channel Fl1 fluorescence intensities with the minimum distribution (% CV) for these microbeads, as measured on dot plots or histograms. Instrument components related to the additional fluorescence channels then may be aligned; this may be accomplished by adjusting the components of these channels to obtain a maximum intensity and minimum distribution while running bright microbeads carrying the dyes that will be used to calibrate those specific fluorescence channels.

(2) Setting Target Conditions

After fully aligning the flow cytometer, the laser power and photomultiplier (PMT) voltages are adjusted so that the sample (e.g., blood) appears in optimal positions in all four parameters (e.g., forward scatter, side scatter, green fluorescence, and red fluorescence). "Optimal positions" means that all populations of interest in the sample for each parameter are completely visible on the appropriate screen of the flow cytometer. The optimal positions of these four parameters are together termed the "target conditions" when the flow cytometer is completely adjusted.

The target conditions may vary between sample types or patient groups, e.g., AIDS, leukemia, organ transplant, cell culture line, etc. For example, for lymphocytes, in normal lysed whole blood measured on a FASCcan TM flow cytometer (Becton Dickinson & Co., Mountain View, Calif.), the following settings are an example of settings that might be used a) forward scatter set with a detector, E00, and amplifier, 2.00; b) side scatter, PMT voltage of 340 with amplifier at 1.00; c) Fl1 of 640 volts and amplifier log; d) Fl2 PMT of 580 volts and amplifier log; and e) laser power of about 500 mW.

(3) Determining Target Channels

The microbead reference standard is run on the flow cytometer under the same instrument settings for laser power and photomultplier voltages as were previously determined in setting the target conditions to determine the peak channels for the four parameters of the microbead population. A "peak channel" is generally taken as the median channel in the series of channels comprising the peak when the parameter reading is plotted vs. the channel number.

(4) Re-establishing the Target Conditions

When the flow cytometer is used on the same sample type or patient group, after being shut off or after it has been used for other types of samples, the appropriate microbead reference standard is again run on the flow cytometer, and the laser power and PMT settings adjusted so that the peak channels of the microbeads falls in the target channels as determined above.

(5) Quality Assurance

The laser power and PMT voltages are plotted on Levy Jennings charts to indicate instrument performance by showing variations over time which may be isolated (spikes) or trends (at least three consecutive points varying in one direction from the mean). The usual acceptable range in the Levy-Jennings plot is two standard deviations. Greater trend variation indicates flow cytometer performance problems.

The features and advantages of the present invention are more fully shown with respect to the following non-limiting examples.

EXAMPLE I

A population of microbeads 7.5u in diameter and having a coefficient of variation of diameter of 2.0% and containing surface carboxyl groups (see co-pending application Ser. No. 07/374,435) were activated with water-soluble 1-ethyl-3-(3-dimethylaminopropyl) carbodiimide to bind avidin, in turn labeled with biotinated R-phycoerythrin at an intensity of approximately 250,000 molecules of equivalent soluble fluorochrome per microbead (MESF). The microbeads were reacted with fluorescein isothiocyanate (FITC) according to the procedure of the co-pending application to a level of approximately 200,000 MESF. The coefficient of variation of each parameter (forward scatter, Fl1 and Fl2) in this bead population was less than 10%. This population of microbeads was termed the dual-labeled microbead reference standard.

EXAMPLE II

To determine target conditions, a FACScan TM flow cytometer was used, having an air cooled argon laser tuned to an excitation wavelength of 488 nanometers (nm) and fitted with a 520–550 nm bandpass filter on the green fluorescence channel Fl1, and a 565 nm longpass barrier filter on the red fluorescence channel Fl2, with log amplifiers on the fluorescence channels. Count rates were kept to approximately 500 per second.

Figure 7:
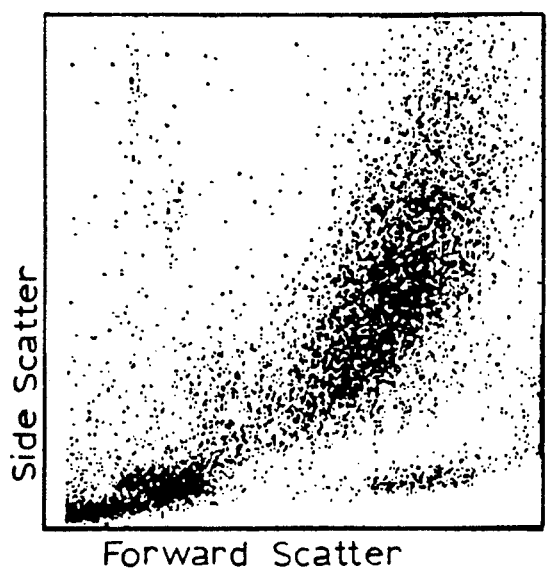
FIG. 7 is dot plot of the desired forward vs. side scatter of lysed whole human blood adjusted according to Example II.
Figure 8:
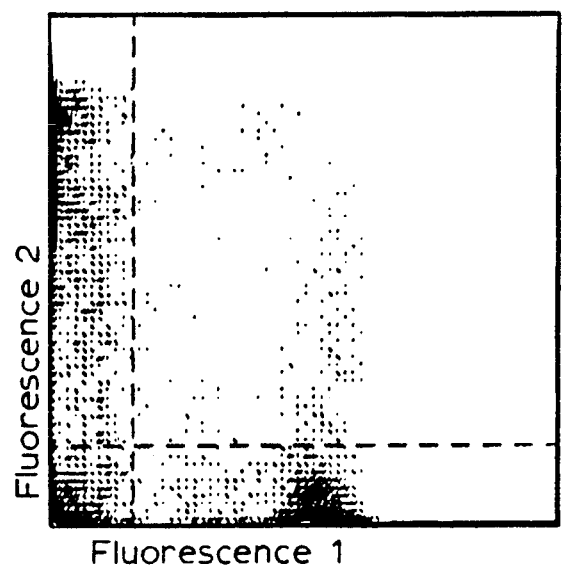
FIG. 8 is a dot plot of the desired Fl1 green fluorescence vs Fl2 red fluorescence of dual-labeled lymphocytes according to Example II.

The flow cytometer was adjusted as discussed above under "Setting Target Conditions" so that a sample of normal human whole blood lysed to remove erythrocytes and stained with Leu 3a-FITC conjugated monoclonal antibody and Leu 2a-PE conjugated antibody (see copending application) presented dot plots for forward vs. side scatter as shown in FIG. 7, and Fl1 green vs Fl2 red as shown in FIG. 8.

EXAMPLE III

Figure 9:
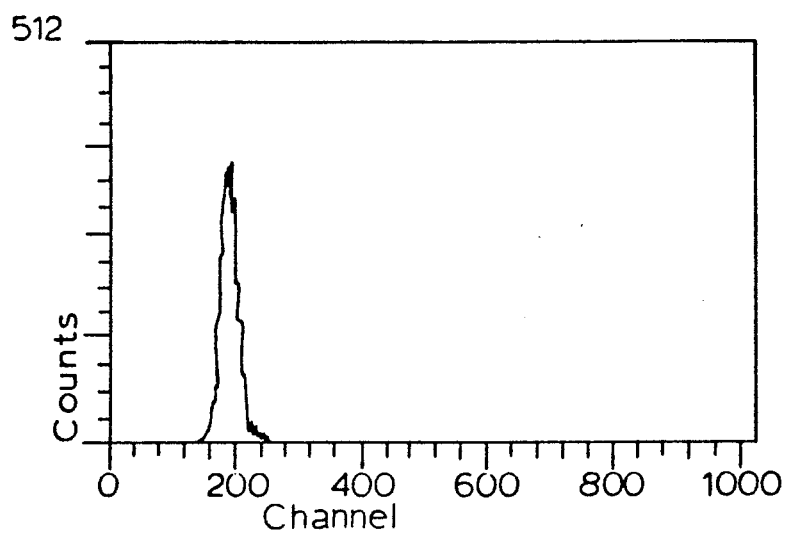
FIG. 9 is a histogram of the forward scatter parameter of the dual-labeled microbeads according to Example III showing counts on the flow cytometer vs. channel.
Figure 10:
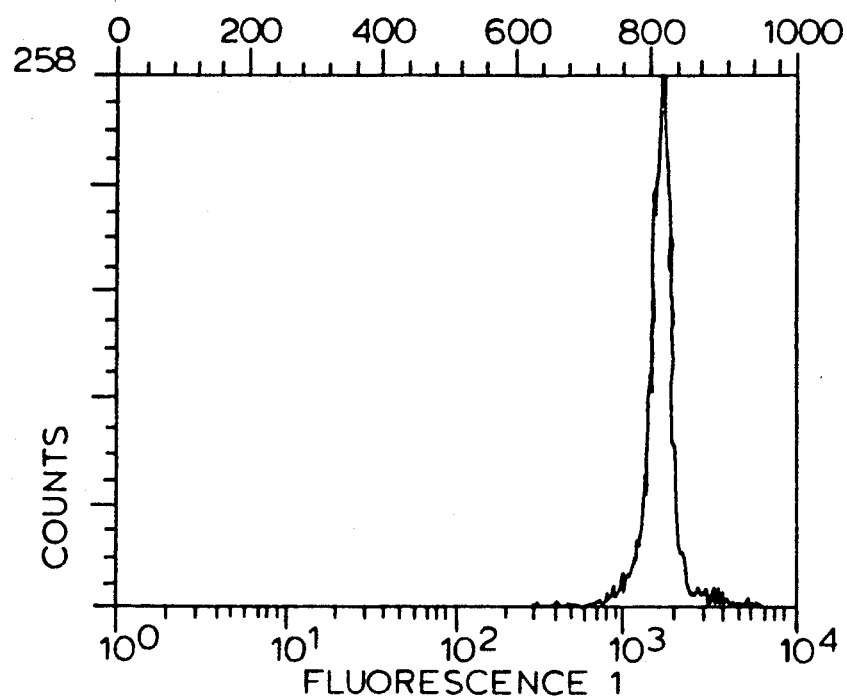
FIG. 10 is a histogram of the green fluorescence parameter (Fl1) of the dual-labeled microbeads according to Example III.
Figure 11:
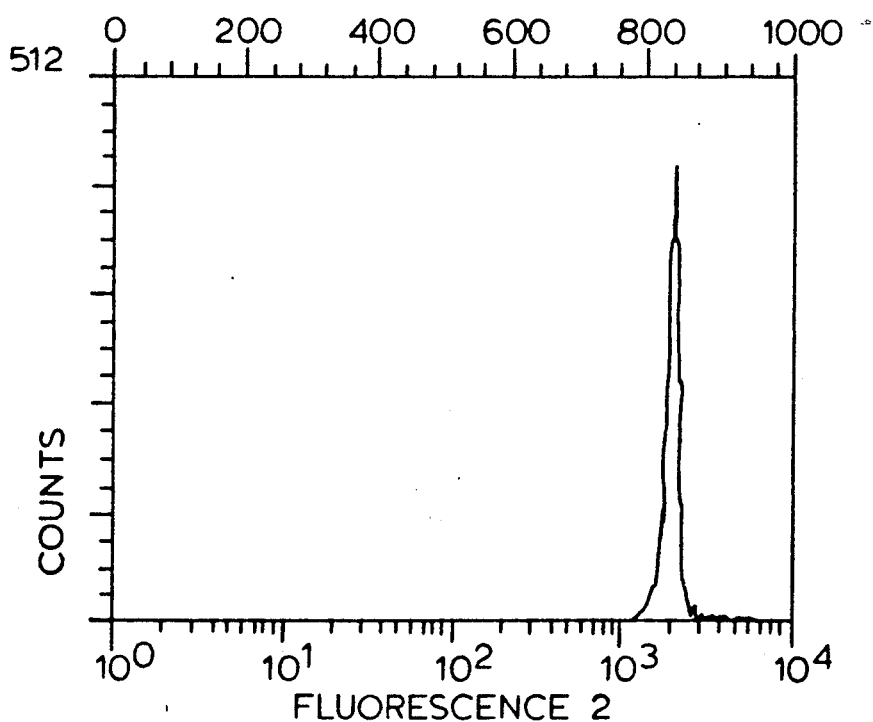
FIG. 11 is a histogram of the red fluorescence paramater (Fl2 of the dual-labeled microbeads according to Example III.

To determine target channels, the dual-labeled microbead reference standard prepared according to Example I was run under the same instrument conditions as in Example II and the peak channels for the forward scatter, Fl1, and Fl2 parameters were determined and the results are shown in FIGS. 9–11. The peak channels for these parameters were channels 193, 832 and 842, respectively.

EXAMPLE IV

With the compensation circuits turned off, the peak channels for Fl1 and Fl2 were 833 and 842, respectively, With the circuits adjusted correctly (Fl1 minus %Fl2=0.8; and Fl2 minus %Fl1=29.0), the peak channels of the dual-labeled reference beads were 831 and 842. Furthermore, with the compensation circuits adjusted higher than the correct compensation values (i.e., Fl1 minus %Fl2=2.0; and Fl2 minus %Fl1=50.0), the corresponding peak channels of the reference beads were 830 and 840. Thus, under normal conditions as well as at considerable variations therefrom, there was no significant effect of compensation adjustments on target channels. However, if the Fl1 minus %Fl2 is adjusted to 10.0, the position of the microbead standard in the Fl1 channel dropped to 150.

EXAMPLE V

After performing a determination of target conditions (Example II) and target channels (Example III), the flow cytometer was shut off, and then turned on again. The microbead reference standard from Example I was run on the flow cytometer and the instrument adjusted such that the microbeads fell in the target channels determined from Example III. Upon running the same blood sample as used in Example II, it was found that the scatter and fluorescence dot populations and peaks of the blood cells were identical to those in Example II. Results such as these with labeled microbeads according to the invention show that use of the microbead reference standard allows flow cytometer adjustment so that reproducible, repeatable results may be obtained with a sample.

While the invention has been described with reference to specific embodiments and compositions, it will be appreciated that numerous modifications, variations and embodiments are possible, as being within the spirit and scope of the invention.

What is claimed is:

1. A microbead reference standard for adjustment of a flow cytometer, for subsequent measurement of a selected sample, said sample selected from the group consisting of cells and particles, said sample labeled with at least two fluorescent dyes, said dyes selected from the group consisting of fluorescein, phycoerythrin, allophycocyanine, propidium iodide, the fluorochrome Hoescht 33342, and a sulfonyl chloride derived from sulforhodamine 101, using multiple fluorescence channels of the flow cytometer, said standard comprising a population of microbeads, wherein each of said microbeads:

(a) is labeled with at least two fluorescent dyes that are the same, and have the same excitation and emission spectra, as the dyes with which the sample is labeled so that the dyes on the microbeads have fluorescence intensity levels registerable in multiple fluorescent channels of a flow cytometer, said dyes selected from the group consisting of fluorescein, phycoerythrin, allophycocyanine, propidium iodide, the fluorochrome Hoescht 33342, and a sulfonyl chloride derived from sulforhodamine 101;

(b) is of substantially similar size, said microbead population having a coefficient of variation of diameter of about 2% or less; and (c) is substantially equivalent in size to the fluorescently labeled sample, wherein the microbeads allow reproducibility of data to be obtained which is independent of specific flow cytometer and time frame of data measurement and compensation of the flow cytometer.

2. A microbead reference standard according to claim 1, wherein the diameter of the microbeads is within the range from about 2 to about 20 microns.

3. A microbead reference standard according to claim 2, wherein the diameter of the microbeads is about 7.5 microns.

4. A microbead reference standard according to claim 1, wherein the fluorescent dyes comprise fluorescein and phycoerythrin.

5. A microbead reference standard according to claim 1, wherein the fluorescent dyes comprise allophycocyanine and fluorescein.

6. A microbead reference standard according to claim 1, wherein one of the fluorescent dyes is incorporated into the body of the microbeads.

7. A microbead reference standard according to claim 6, wherein the fluorescent dyes comprise a sulfonyl chloride derived from sulforhodamine 101 and Hoechst 33342, the sulfonyl chloride derived from sulforhodamine 101 dye is attached to the surface of the microbeads, and the Hoechst 33342 is incorporated into the body of the microbeads.

8. A microbead reference standard according to claim 6, wherein the fluorescent dyes comprise fluorescein and propidium iodide, said fluorescein is attached to the surface of the microbeads, and said propidium iodide is incorporated into the body of the microbeads.

9. A microbead reference standard according to claim 6, wherein the fluorescent dyes comprise Hoechst 33342 and fluorescein, said fluorescein is attached to the surface of the microbeads, and said Hoechst 33342 is incorporated into the body of the microbeads.

10. A microbead reference standard kit comprising a container means enclosing said microbeads of claim 1.

11. A method of adjusting a flow cytometer to obtain reproducible results for a selected sample type, said sample selected from the group consisting of cells and particles, said sample labeled with at least two fluorescent dyes, said dyes selected from the group consisting of fluorescein, phycoerythrin, allophycocyanine, propidium iodide, the fluorochrome Hoescht 33342, and a sulfonyl chloride derived from sulforhodamine 101, said method comprising the steps of:

(a) aligning the flow cytometer;

(b) determining target conditions by adjusting the laser power and photomultiplier voltages and compensation settings of the flow cytometer so that the sample appears in optimal positions in the scatter and fluorescence parameters;

(c) providing a microbead reference standard comprising:

(i) a population of microbeads, each of said microbeads labeled with at least two fluorescent dyes, said dyes being the same dyes as the dyes with which the sample is labeled; each of said microbeads having the same excitation and emission spectra as the sample; each of said microbeads substantially equivalent in size to the fluorescently labeled cells or particles of the sample; said microbead population having a coefficient of variation of diameter of about 2% or less, and characterized by fluorescence intensity levels registerable in multiple fluorescent channels of a flow cytometer, said dyes selected from the group consisting of fluorescein, phycoerythrin, allophycocyanine, propidium iodide, the fluorochrome Hoescht 33342, and a sulfonyl chloride derived from sulforhodamine 101; and (d) determining target channels by running the microbead reference standard on the flow cytometer under the laser power and photomultiplier voltages determined in step (b); and (e) at a time subsequent to step (d), re-establishing target conditions on the flow cytometer on the same sample type by running the microbead reference standard on the flow cytometer and adjusting the laser power and photomultiplier voltages and compensation setting sot hat peak channels for the microbeads are the same as the target channels of step (d), wherein reproducibility of data is obtained which is independent of specific flow cytometer and time frame of data measurement and compensation of the flow cytometer.

12. A method of adjusting a flow cytometer according to claim 11, further comprising re-establishing target conditions on the flow cytometer on said selected sample type by running the microbead reference standard on the flow cytometer at a time subsequent to the determination of said target conditions, and adjusting the laser power and photomultiplier voltages so that said peak channels for the microbeads are the same as the said target channels of step (d).

13. A method of adjusting a flow cytometer according to claim 11, wherein the diameter of the microbeads is within the range from about 2 to about 20 microns.

14. A method of adjusting a flow cytometer according to claim 11, wherein the fluorescent dyes comprise fluorescein and phycoerythrin.

15. A method of adjusting a flow cytometer according to claim 11, wherein the fluorescent dyes comprise allophycocyanine and fluorescein.

16. A method of adjusting a flow cytometer according to claim 11, wherein one of the fluorescent dyes is incorporated into the body of the microbeads.

17. A method of adjusting a flow cytometer according to claim 16, wherein the fluorescent dyes comprise a sulfonyl chloride derived from sulforhodamine 101 and Hoechst 33342, the sulfonyl chloride derived from sulforhodamine 101 is attached to the surface of the microbeads, and the Hoechst 33342 is incorporated into the body of the microbeads.

18. A method of adjusting a flow cytometer according to claim 16, wherein the fluorescent dyes comprise fluorescein and propidium iodide, said fluorescein is attached to the surface of the microbeads, and said propidium iodide is incorporated into the body of the microbeads.

19. A method of adjusting a flow cytometer according to claim 16, wherein the fluorescent dyes comprise Hoechst 33342 and fluorescein, said fluorescein is attached to the surface of the microbeads, and said Hoechst 33342 is incorporated into the body of the microbeads.

* * * * *